United States Patent [19]

Lavender

[11] 4,375,415
[45] Mar. 1, 1983

[54] DEVICE AND METHOD FOR CONTINUOUSLY FRACTIONATING BLOOD TO PRODUCE PLASMA

[76] Inventor: Ardis R. Lavender, Clarks Summit, Pa. 18411

[21] Appl. No.: 265,104

[22] Filed: May 18, 1981

Related U.S. Application Data

[63] Continuation of Ser. No. 743,593, Nov. 22, 1976, abandoned.

[51] Int. Cl.³ .................. B01D 13/00; B01D 31/00
[52] U.S. Cl. .................. 210/651; 210/321.1; 210/433.2; 210/456
[58] Field of Search .......... 210/408, 409, 456, 637, 210/649, 650, 651, 321, 433.2, 927; 55/16, 158; 422/48

[56] References Cited

U.S. PATENT DOCUMENTS

| | | | |
|---|---|---|---|
| 2,247,143 | 6/1941 | Bailey | 210/637 |
| 3,211,645 | 10/1965 | Ferrari | 210/637 |
| 3,238,703 | 3/1966 | Straschil et al. | 55/158 |
| 3,342,729 | 9/1967 | Strand | 210/638 |
| 3,695,446 | 10/1972 | Lyall et al. | 210/321.1 |
| 3,721,623 | 3/1973 | Stana | 210/639 |
| 3,819,742 | 6/1974 | Brun et al. | 210/651 X |
| 3,974,068 | 8/1976 | Ebner et al. | 210/637 |
| 3,984,324 | 10/1976 | Wang | 210/232 |

Primary Examiner—David R. Sadowski
Attorney, Agent, or Firm—Dithmar, Stotland, Stratman & Levy

[57] ABSTRACT

An apparatus, system and process for continuously fractionating blood in which blood from a donor is passed along a semipermeable membrane through which passes a fraction to be collected. Turbulent blood flow is maintained to prevent a filter cake from building up on the membrane surface and thereby prevent the blood fraction from passing therethrough. The system includes the blood fractionator, a collection apparatus, a blood pump and appropriate blood clot filters. The rapid blood fraction production rate and the small size of the device facilitates in situ collection of the blood fraction. Fractionation rates upwards of 30 volume percent of blood flow are possible.

51 Claims, 6 Drawing Figures

DEVICE AND METHOD FOR CONTINUOUSLY FRACTIONATING BLOOD TO PRODUCE PLASMA

RELATED APPLICATIONS

This application is a continuation of Ser. No. 743,593 filed Nov. 22, 1976, abandoned.

BACKGROUND OF THE INVENTION

Blood fractionating is quite useful since human blood is a complex mixture of red blood cells, white cells and platelets suspended in a liquid plasma. The plasma, about 55 percent by volume of the blood, is a solution of water, salts and proteins. Each of the blood fractions is useful individually and in various combinations and therefore, apparatus, systems and methods for fractionating blood are common.

Blood plasma has particular use for diagnosis and therapy, either as whole plasma or as plasma proteins. Currently, plasma is obtained from human donors by a time consuming and rather cumbersome process. A needle is inserted into a donor's vein and about 500 milliliters of blood are removed during a time span of 15 to 20 minutes. The bag containing the blood is removed and centrifuged and the supernatant plasma is removed to another container, the cells being returned thereafter to the donor. The total time required to draw the blood, produce the plasma and reinfuse the red blood cells, is about 90 minutes. The process includes several risks including the accidental return of another person's blood to the donor, an accident which may be fatal, as well as providing multiple opportunities for infection.

Various apparatus and systems have been proposed for the collection of blood plasma; however, none has proved satisfactory and none is in commercial use. Such systems are described in U.S. Pat. No. 3,705,100, issued to Blatt et al., Dec. 5, 1972, for: *BLOOD FRACTIONATING PROCESS AND APPARATUS FOR CARRYING OUT SAME*, and in U.S. Pat. No. 3,788,319, issued to Gillette, Jan. 29, 1974, for, *SYSTEM FOR EXCHANGING BLOOD ULTRAFILTRATE*. The Blatt et al. device has several disadvantages, not the least of which is the extremely slow plasma production rate. The Gillette patent discloses a device, but includes neither construction details, nor operational data.

SUMMARY OF THE INVENTION

This invention relates to an apparatus, system and process for continuously fractionating blood and more particularly to apparatus, systems and processes for continuously producing plasma in situ from a blood donor.

An important object of the present invention is to provide apparatus, systems, and processes for continuously fractionating blood in which turbulent blood flow is provided along a semipermeable membrane sufficient to prevent caking on the membrane and to produce a blood fraction therethrough at a rapid rate.

Another important object of the present invention is to provide an apparatus, system and process of the type set forth in which the blood flow path across the membrane is short and the blood fraction collected is up to thirty volume percent of the blood flow.

Another object of the present invention is to provide an apparatus for continuously fractionating blood comprising a housing having a blood inlet adapted to be connected to a blood source and a blood outlet in fluid communication with the blood inlet and a blood fraction outlet, a semipermeable membrane separating the blood fraction outlet from the blood inlet and outlet and permitting a blood fraction to pass therebetween, and means providing turbulent blood flow along the membrane to maintain the membrane sufficiently cake free for passage of the blood fraction therethrough, passage of blood from the blood inlet along the membrane to the blood outlet continuously passing the blood fraction through the membrane and out of the blood fraction outlet.

A further object of the present invention is to provide an apparatus of the type set forth wherein the turbulent blood flow along the membrane is provided by mechanism including an apertured plate producing blood jets against the membrane.

A still further object of the present invention is to provide a system for continuously fractionating blood in situ comprising a housing having a blood inlet adapted to be connected to a blood vessel and a blood outlet adapted to be connected to a blood vessel and a blood fraction outlet adapted to be connected to a collecting means, a semipermeable membrane separating the blood fraction outlet from the blood inlet and outlet and permitting a blood fraction to pass therebetween, means including blood flow accelerating mechanism providing turbulent blood flow along the membrane to maintain the membrane sufficiently cake free for passage of the blood fraction therethrough, passage of blood from the blood inlet to the blood outlet along the membrane continuously providing the blood fraction collected in the collecting means.

Yet another object of the present invention is to provide a process for continuously fractionating blood in situ comprising continuously directing blood from a donor along a blood flow path at least partially defined by one surface of a semipermeable membrane having a pore size from about 0.1 to about 6 microns in diameter, providing turbulent blood flow in the flow path defined by the membrane sufficient to maintain the one surface sufficiently cake free for passage of a blood fraction therethrough, continuously collecting the blood fraction passing through the one surface of the membrane, and continuously directing the remaining blood components back to the donor.

These and other objects of the present invention together with further advantages thereof may be more readily understood when taken in conjunction with the following specification and drawings, in which:

DETAILED DESCRIPTION OF THE PREFERRED EMBODIMENT

Figure 2:
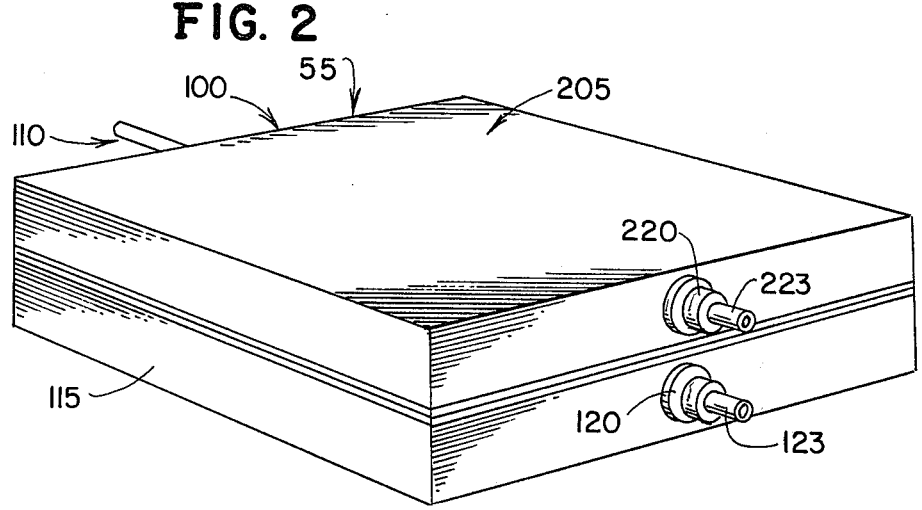
FIG. 2 is a perspective view of the fractionating apparatus.
Figure 1:
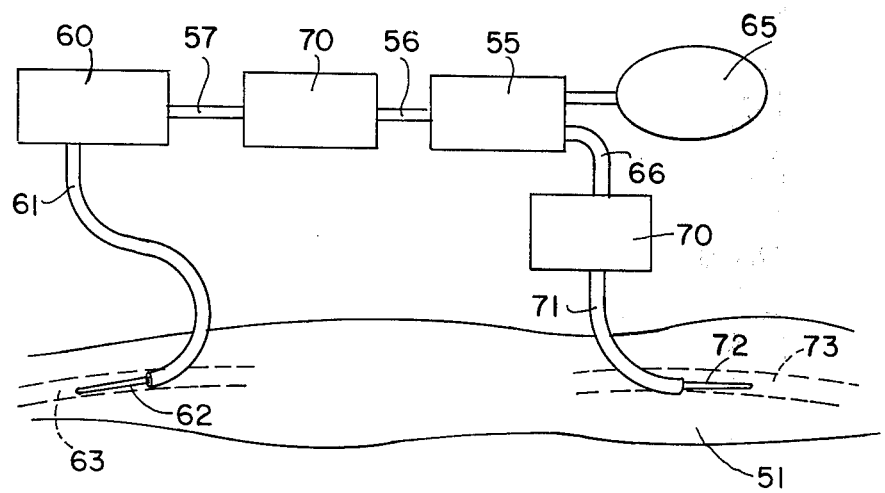
FIG. 1 is a schematic outline of the system of the present invention showing the fractionating device in connection with a blood pump, suitable blood clots filters connected in situ to a blood donor and collection means.

Referring now to the drawings, and in particular to FIG. 1, there is disclosed a system 50 for continuously fractionating blood from a donor 51. The system 50 includes a fractionator 55 connected to the donor 51 by means of a tube 56 connected from the inlet end of the fractionator 55 to a blood clot filter 70 and a tube 57 extends from the other end of the blood clot filter 70 to a blood pump 60, in turn connected by a tube 61 to a needle 62 inserted into a blood vessel 63. A number 14 or 16 gauge needle is commonly used and the blood vessel may be either a vein or an artery, although a vein is preferred. A collection device 65 is connected to the fractionator 55 and collects the blood fraction separated from the donor's blood. A tube 66 connects the blood outlet end of the fractionator 55 to another blood clot filter 70, connected by a tube 71 to a needle 72 inserted into a suitable vessel 73. Blood clot filters 70 are optional depending on the particular circumstances of system 50 use and whether the donor 51 is prone to clotting, as well as other factors known to those skilled in the art. It is readily within the skill of the art to determine whether blood clot filters 70 are necessary and many such filters are available. All of the materials in the system 50 are biocompatible with blood and it is understood that only such matrials are to be used in the system 50.

Roller type blood pumps 60 are commercially available, sufficient to produce a blood flow rate in excess of the range between about 75 and 150 cubic centimeters per minute, the desired range of blood flow in the system 50. Further, collection devices 65, such as plastic bags, are available for the blood fraction to be collected. While the system 50 will be described principally with respect to the collection of blood plasma, it should be understood that the system can easily be used to obtain other blood fractions, such as ultrafiltrates, by adjustment of the membrane in the fractionator 55, as will be explained.

Figure 3:
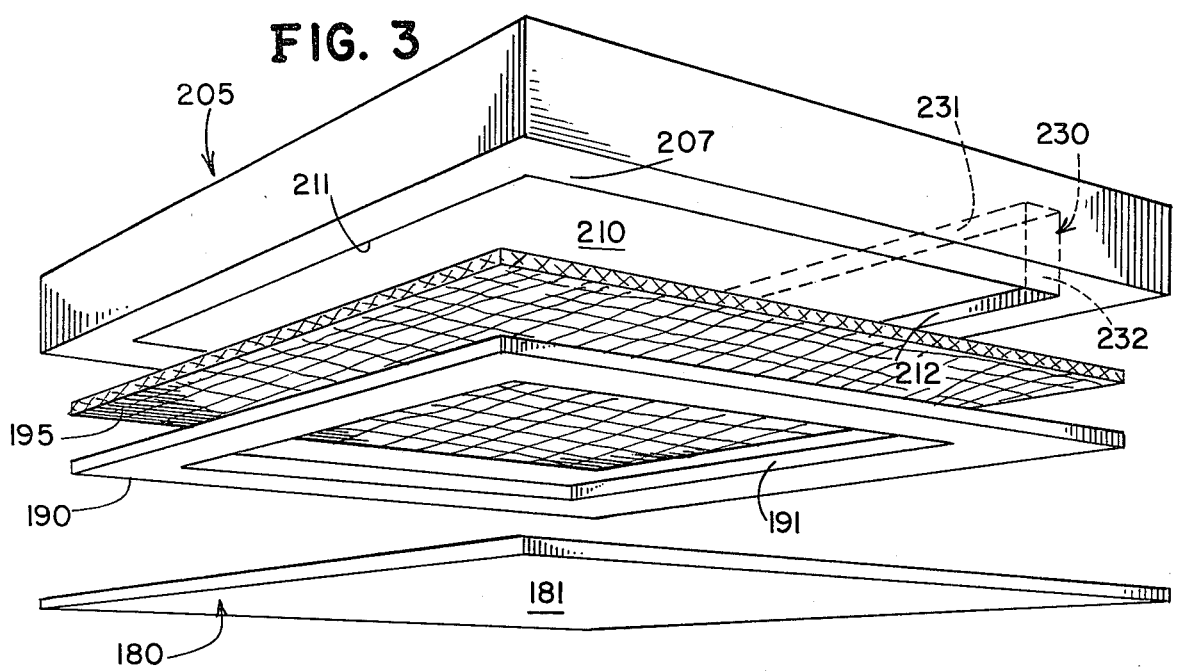
FIG. 3 is an exploded perspective view of the fractionating apparatus illustrated in FIG. 2.
Figure 3:
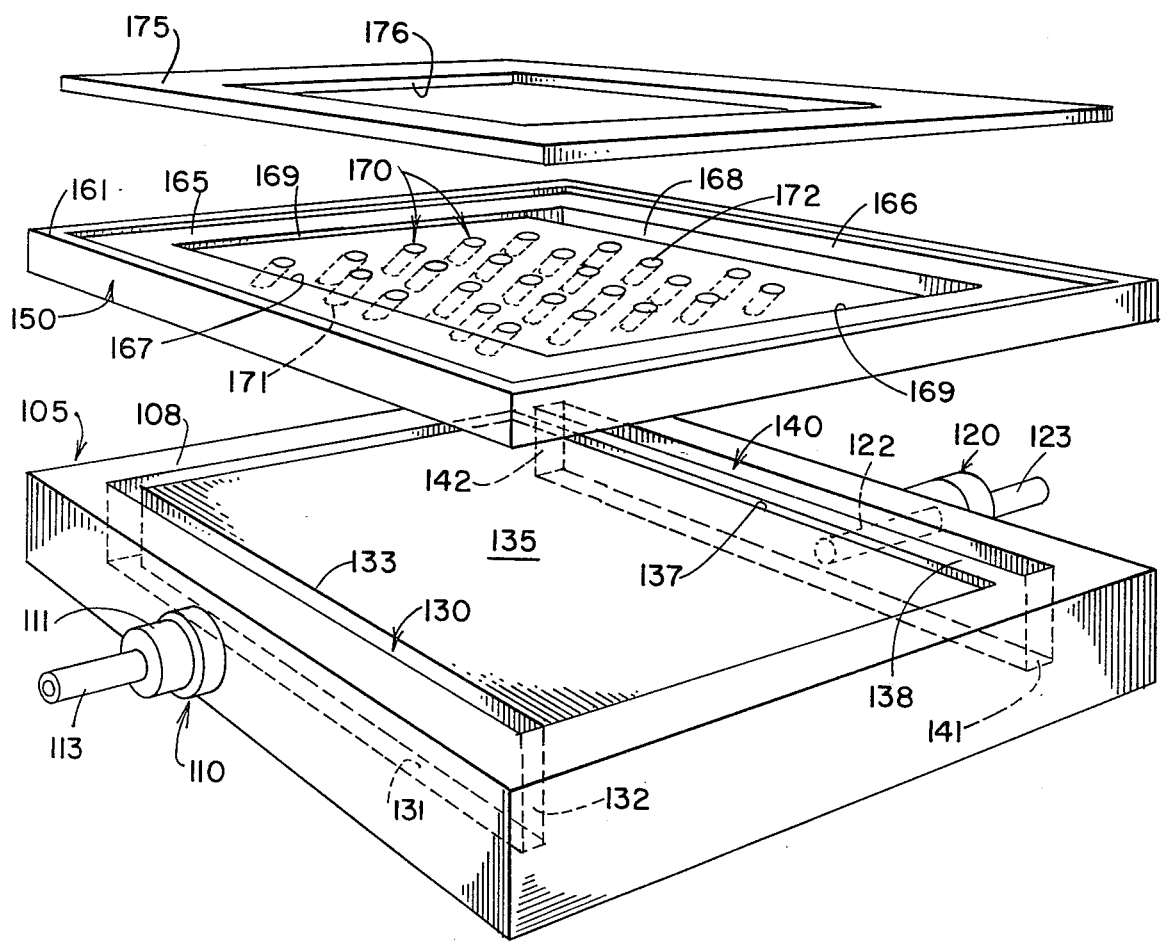
Figure 4:
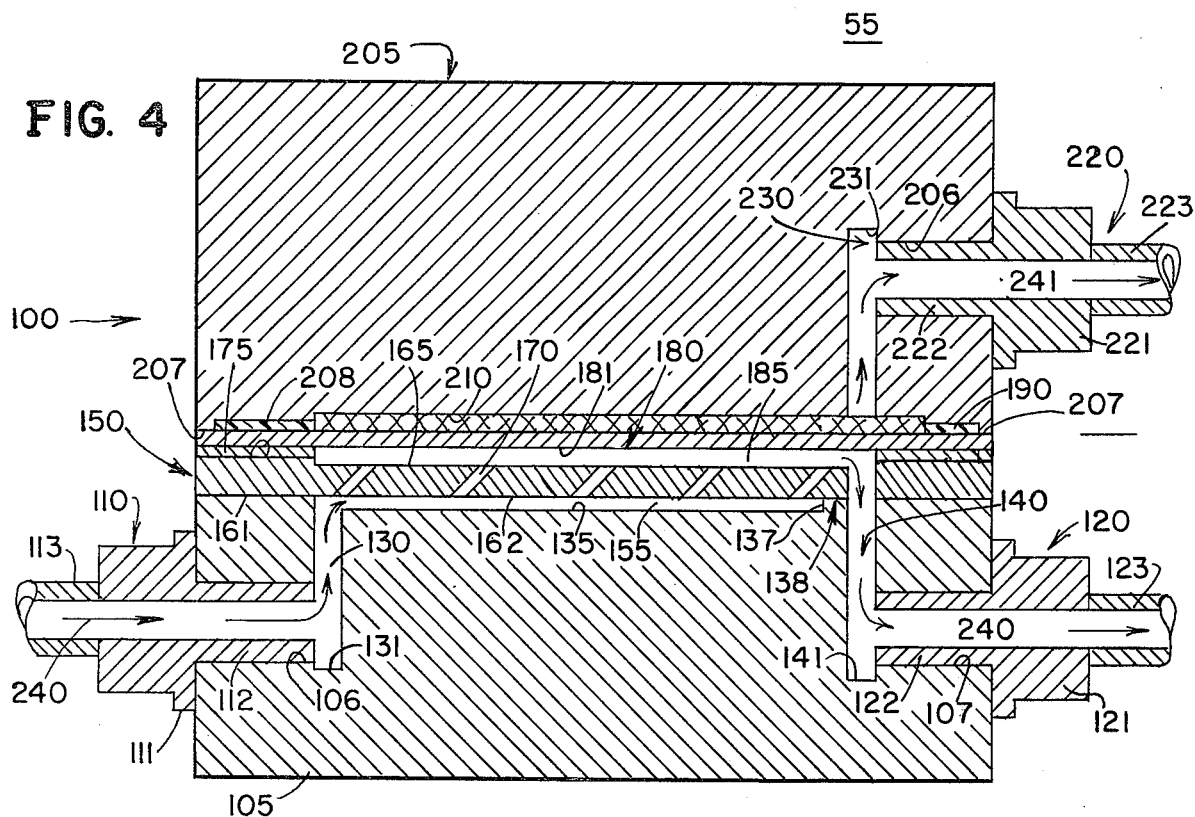
FIG. 4 is a view in section of the fractionating apparatus illustrated in FIG. 2, taken along the line 4—4 thereof.
Figure 5:
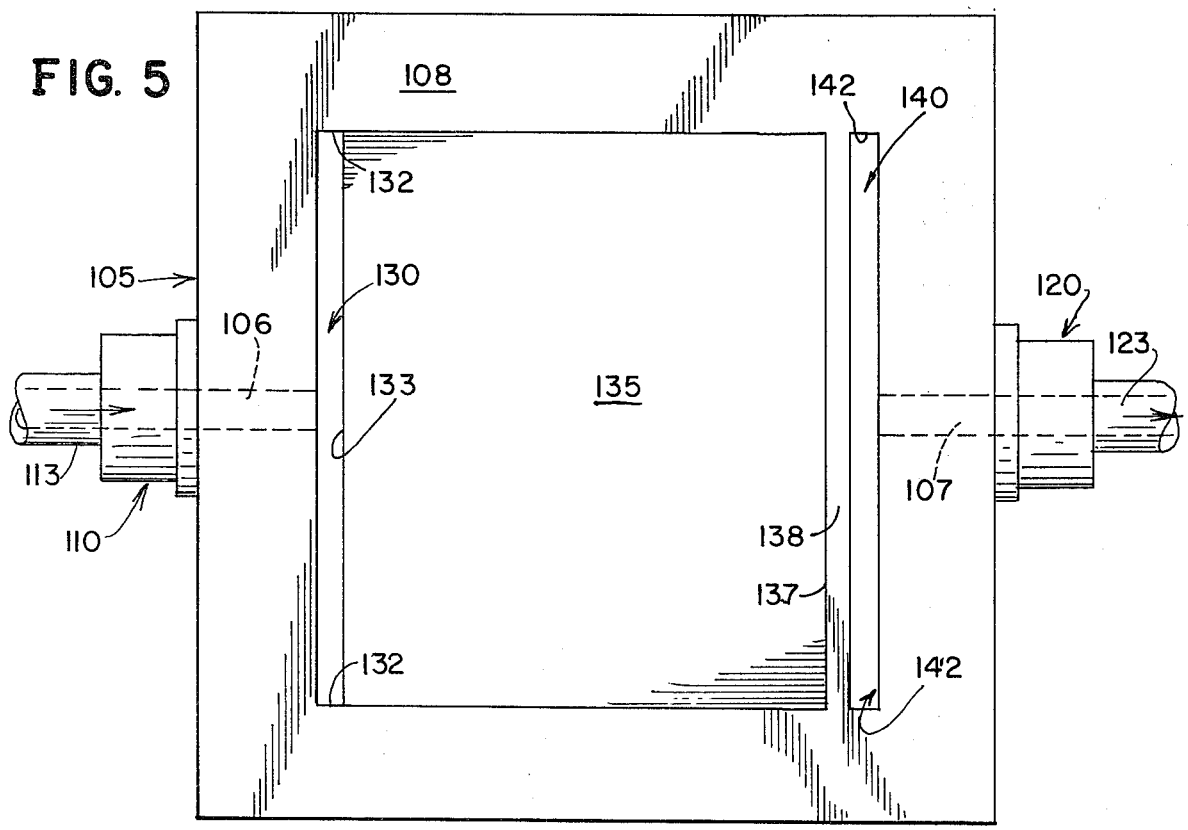
FIG. 5 is a plan view of the lower member of the fractionating apparatus illustrated in FIG. 2.

Referring now to FIGS. 3 through 5, there is disclosed in more detail the fractionator 55 of the present invention, including a housing 100 consisting of a lower member 105 and an upper member 205 in substantial mating relationship. Member 105 has coaxial apertures 106 and 107 at the opposite ends thereof spaced from the inner surface 108 of the member 105. A blood inlet fixture 110 is fixedly inserted in the aperture 106, the fixture comprising a body 111 including an enlarged flange portion exterior to the member 105 and an elongated shank 112 extending into and in sealing relationship with the aperture 106. An elongated tube 113 extends away from the body portion 111 and is adapted to receive a tube 56 thereon. A blood outlet fixture 120 is similarly fitted within the aperture 107, the fixture including an exterior body portion 121 having a shank 122 sealingly disposed within the aperture 107, and an outwardly extending tube 123 adapted to receive the tube 66 thereon.

The inner end of the shank 112 of the blood inlet fixture 110 terminates in a blood inlet manifold 130 disposed in the lower member 105. The blood inlet manifold 130 is a rectangular groove extending transversely of and normal to the axis between the fixture 110 and the fixture 120 and is defined by a bottom wall 131 and opposed upstanding side walls 132. The blood inlet manifold 130 is in fluid communication with the blood inlet fixture 110. A recessed surface 135 is provided in the bottom member 105 and is generally square in configuration. The recess surface 135 extends from the interior end of the manifold 133 to an end 137 spaced inwardly from the blood outlet fixture 120. The recess area, therefore, extends between the edge 133 of the inlet manifold 130 and the distal end 137 forming an upstanding ridge 138. The side boundaries of the recessed surface 135 are defined by the end walls 132 of the inlet manifold 130 and lie in the same spaced apart and parallel planes.

The upstanding ridge 138 bridges the recessed surface 135 and a blood outlet manifold 140 having a bottom 141 and upstanding sides 142. The dimensions of the blood outlet manifold 140 are substantially the same as the dimensions of the blood inlet manifold 130, with the bottoms 131 and 141 respectively lying in the same plane and the side walls 132 and 142 lying in the same planes, respectively.

It should be noted that the top surface of the ridge 138 lies in the same plane as the inner surface 108 of the bottom member 105.

An apertured plate 150 having substantially the same perimeter dimension as the member 105 is positioned on the surface 108 and the top surface of the ridge 138 and extends substantially to the outer end of the member 105. The apertured plate 150 forms with the recessed surface 135 a blood distribution plenum 155. The apertured plate 150 has a top surface 161 and a bottom surface 162, the bottom surface 162 resting on the forming seal with the surface 108 of member 105. The top surface 161 has a recess 165 therein extending from an end wall 167A slightly indented from the adjacent outside surface. A recess 185 in the plate 150 has an edge in alignment with the outer wall of the blood inlet manifold 130 and extends to an end wall 168 in alignment with the outer wall of the blood outlet manifold 140. The recess 185 is defined on the sides by walls 169 in alignment with a plane formed by the end walls 132 and 142 of the manifolds 130 and 140 respectively. An elongated rectangular slot 166 at the end of the recess area 185 extends entirely through the plate 150 and in registry with and of the same peripheral dimension as the outlet manifold 140.

The plate 150 has provided therein a plurality of apertures 170 angularly disposed in the plate 150 each having an inlet end 171 and outlet end 172. The apertures 170 as shown in FIG. 3, are arranged in columns and rows substantially uniformly over the entire recess 165. The apertures 170 are angularly disposed such that the inlet ends 171 thereof are closer to the blood inlet 110 and the outlet ends 172 thereof are closer to the blood outlet 120, blood flowing through the apertures 170 forming forceful jets, for a purpose hereinafter set forth. A gasket 175 rests on the upper surface of recess 165 of the apertured plate 150 and is provided with an opening 176 coextensive with the recess 185 of the plate 150. The gasket 175 may be made of any biocompatible elastomeric resilient material.

A semipermeable membrane 180 having a lower surface 181 thereof is positioned over the gasket 175 and forms with the recess 185 a blood channel 185A. The semipermeable membrane is of the type commercially available from the Gillman Company, the Millipore Company or Nucleopore Corporation. The pore size of the membrane may be between 0.1 and 6 microns depending on the end use of the fractionator 55. The peripheral dimensions of the membrane 180 are substantially the same as the plate 150 and the member 105.

A gasket 190 having a opening 191 therein is positioned over the membrane 180, the opening 191 being somewhat larger than the opening 176 in the gasket 175, for a purpose hereinafter set forth. A membrane support 195 is positioned inside the gasket 190 to maintain constant the transverse dimensions of the blood channel 185A and prevent deflection of the membrane 180 out of its normal plane. The membrane support 195 may consist of a woven mesh, or a plate having ridges, pyramids or cones.

An upper member 205 having the same general peripheral dimensions as the member 105 is positioned over the membrane support 195. The upper member 205 is provided with an aperture 206 in the end thereof in registry with the outlet end of the lower member 105 and of the same general dimension as the apertures 106 and 107 in the lower member 105. The upper member 205 has an inner surface 207 and a recess 208 for the gasket 190, the recess 208 being wider at the inlet end of the upper member 205 than at the outlet end for a reason to be explained. A recess 210 in the inner surface 207 of the member 205 defines a blood fraction cavity and has the same transverse dimensions as the recess 135 in the member 105 and has the end 211 thereof in alignment with the outer wall of the blood inlet manifold 130 and has the other end 212 thereof extending beyond the outer wall of the outlet manifold 40. Since the membrane support 195 is positioned within the blood fraction cavity 210, the membrane support extends beyond the outlet manifold 140 in the member 105 and provides support for the membrane 180 in contact therewith beyond the point which blood contacts the membrane.

A blood fraction outlet fixture 220 is positioned in the aperture 206, the fixture 220 being identical in construction to the fixtures 110 and 120 and having a body portion 221 outside the member 205 and an elongated shank 222 sealingly disposed in the aperture 206. An exterior tube 223 is adapted to receive a tube thereon. The fixture 220 provides communication between the outside of the fractionator 55 and a blood fraction outlet manifold 230 having substantially the same dimensions as the manifolds 130 and 140 and including a top wall 231 and end walls 232, the top wall 231 being parallel to the bottom wall 131 and 141 of the manifolds 130 and 140, respectively and the end walls 232 being respectively aligned with the end walls 142 of the outlet manifold 140.

The member 205 is sealingly connected to the member 105 by ultrasonic welding, silicone rubber adhesives or any suitable art recognized means. When sealed together, the member 105 and 205 provide a fluid tight blood flow path illustrated by the arrows 240 in FIG. 4, and a blood fraction path 241. Blood entering the blood inlet 110 flows through the fixture into the manifold 130 and to the blood distributing plenum 155 formed between the recess 135 in the member 105 and the bottom surface 162 of the apertured plate 150. Blood in the plenum 155 flows through the apertures 170 into the blood channel 185A and impinges against the surface 181 of the semipermeable membrane 180. Since flow is turbulent, the blood contact with the membrane 180 is sufficient to prevent caking on the surface 181 and enables the desired fraction to pass through the semipermeable membrane into the blood fraction cavity 210 and thence, into the manifold 230 and out of the fixture 220. Simultaneously, blood exits the blood flow channel 185 through the slot 166 in the apertured plate 150 into the blood outlet manifold 140 and thence, out of the fractionator 55 through the fixture 120.

When utilized in system 50, it is apparent that the fractionator 55 provides continuous production of a blood fraction through the fixture 220 while blood from a donor 51 is continuously removed from one blood vessel 63 and reintroduced into another blood vessel 73, all without the necessity of removing the blood from the donor, mechanically treating it and then returning the blood with the attendant possibilities of error and infection.

Figure 6:
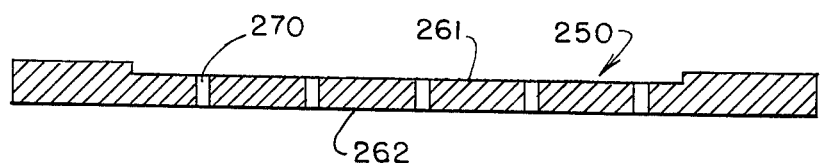
FIG. 6 is an alternate embodiment of the apertured plate used in connection with the apparatus disclosed in FIG. 2.

Referring to FIG. 6, there is disclosed a second embodiment of the apertured plate 150, the second embodiment 250 providing opposed surfaces 261 and 262 interconnected by a plurality of apertures 270 each being perpendicular to the planes of the surfaces 261 and 262. The plate 250 is an alternative to the previously described plate 150 and performs to provide turbulent blood flow along a membrane surface 181.

In a constructional example, the members 105 and 205 were made of methylacrylate and fitted with standard fixtures 110, 120 and 220. The members were 1.74 inches square and had a total thickness of ⅜ inch thick. Each of the manifolds 130, 140 and 230 were 0.296 inches deep and 0.0625 inches wide. The vertical dimensions of the blood distributing plenum 155 and the blood fraction collection plenum or cavity 210, were 0.015 inches or 15 mils. The plate 150 was polymethylacrylate having a thickness of about 30 mils; and 25 apertures 270 were drilled therein each having a diameter of 16 mils. A Nucleopore membrane 180 having a pore size of 3 microns and in another example, having a pore size of 5 microns was used, and the gaskets 175 and 190 were silicone rubber. The membrane support was a polyester woven fabric having a thickness of 15 mils.

Devices of the type described have fractionated various liquids. For instance, an artificial blood liquid consisting of 6 microns diameter yeast cells in India ink solution was pumped through a fractionator 55 of the type described and produced cell-free filtrate. Flow rates of up to 450 milliliters per minute produced filtrate rate at 30 milliliters per minute and continuous use did not result in either a decreasing filtrate rate per production or any yeast cells in the filtrate.

Cows blood has also been tested and red blood cell-free plasma has been continuously produced by the fractionator 55. Cows blood has red blood cells measuring between about 3 and 6 microns as compared to red blood cells in human blood of between about 7 and 9 microns. Since the pore size of the membrane must be smaller to produce blood plasma from cows blood than from human blood, the transmembrane pressure gradient will be larger. Therefore, the operating parameters for production of plasma will be less severe for human blood than for cows blood.

At flow rates of 100 milliliters per minute, the calculated linear velocity of blood through the apertures 170, 270 or plate 150 in fractionator 55 is about 51 centimeters per second, the preferred linear velocity for producing plasma being in the range of from about 40 centimeters per second to about 80 centimeters per second, and the desired flow rate for human use in any event, being in the range of between 75 milliliters per minute and 150 milliliters per minute. Blood fractions produced by the fractionator 55, can be in the area of between about 20 and about 30 volume percent of the blood flow rate through the fractionator. Therefore, for blood flow at the rate of 100 milliliters per minute, the blood fraction would be between about 20 and about 30 milliliters per minute, thereby producing, in 20 minutes, between about 400 and about 600 milliliters of plasma.

The linear velocities used in the fractionator 55 are intentionally high to insure the blood flow along the surface 181 of the semipermeable membrane 180 (that is in the blood channel 185A) is turbulent. It is believed that the turbulent, high velocity blood flow along the membrane 180 prevents the expected caking of blood on the surface 181, thereby maintaining relatively constant blood fraction or filtrate production. The blood jets provided by the apertures 170, 270 also produce a shear force along the membrane surface 181, which may be critical. There is a vector normal to membrane 180 which transfers kinetic to pressure energy and is important to operation of the device. Conversion from kinetic to pressure energy increases production rate of blood fraction. In any event, operation of the fractionator 55 at high blood flow rates, and high linear velocity along the membrane 180, contrary to expectations, does not plug the membrane, but maintains the membrane cake free and preserves the plasma (or blood fraction) production rate. This surprising result is contrary to expectations and previous devices requiring relatively slow laminar flow along the membrane surface.

As is understood, during fractionation, the red blood cell concentration increases from the blood inlet fixture 110 to the outlet fixture 120 with the simultaneous increase in blood viscosity. For humans, a 60% red blood cell concentration in the blood exiting the fractionator 55 is the upper limit desirable. With the blood fraction being between about 20 and about 30 percent by volume of the blood flow rate, the blood flow rates for human donors are limited to a minimum between 75 and 100 milliliters per minute, to prevent red blood cell concentrations from exceeding the 60% limit. Lower blood flow rates are acceptable provided the blood fraction production rate is lower. The fractionator 55 can operate at flow rates in excess of 450 milliliters per minute, and red blood cell concentration is correspondingly decreased at the outlet of fractionator 55.

Since the fractionator 55 depends on the transfer of a blood fraction through the membrane 180, it is important for good efficiency to maintain the blood flow path 185A dimensionally stable and relatively thin. In the devices actually built, the blood flow path 185A had a dimension measured transversely from the membrane surface 181 of about 16 mils, it generally being preferred that the blood flow path be maintained at a thickness of less than about 20 mils. Constructing a blood flow path 185A having a greater dimension than about 20 mils, measured transversely to the membrane surface, will not result in an inoperative device, but merely one having a lower efficiency, since caking of blood cells will be greater on the membrane surface 181.

Another important feature of the present invention, in addition to the relatively high blood fraction output in the order of between about 20% and 30% by volume of the blood throughput, is the short flow path from the blood flow inlet 110 to the blood outlet 120. By maintaining the blood flow path short that is, in the order of about 4 inches or less, trauma to the blood will probably be less than if it were exposed to flow paths greater in length. In the device as presently constructed, the blood flow path from inlet 110 to outlet 120, is less than about 2 inches.

Since it is desirable to maintain uniform flow resistance in the fractionator 55, it is preferred that the blood inlet manifold 130 and the blood outlet manifold 140 have the same dimensions. In the devices constructed, the manifolds were about 20 times deeper, than the blood distribution plenum 155, although manifolds 10 times deeper than the blood distribution plenum would be sufficient. An additional reason for maintaining the blood flow path 185A dimensionally stable is that simultaneously the flow resistance is maintained uniform.

While the semipermeable membranes 180 described herein are relatively thin materials, on the order of 1 to 10 microns thick, other materials may be substituted therefor. Any material which acts as a semipermeable membrane, that is, permits a liquid fraction to flow therethrough while preventing another fraction from flowing therethrough will be satisfactory. Specifically, if the transverse strength of the semipermeable membrane 180 is sufficient to prevent flexure thereof into the cavity 210 (thereby preventing rupture) and at the same time maintaining constant the dimensions of the blood flow channel 185A, and hence the blood flow resistance, no membrane support 195 is required. Absence of the membrane support 195 slightly alters the specific gasket design, but is within the concept of the present invention.

As hereinbefore stated, any biocompatible material will suffice for the present system 50. For instance, plastic collection bags 65 are commercially available and are biocompatible. The material used for the housing 100 was polymethylmethacrylate and this material was also used for the apertured plate 150. Alternatives acceptable are polycarbonates, polypropylenes, polyethylenes and other art recognized materials. The gasket material used in the fractionator 55 was silicone rubber, but other resilient elastomers are available and may be substituted. The membrane support 195 was a Dutch weave polyester; however; many other alternatives are available.

An additional feature not hereinbefore disclosed of the present invention, is the ability thereof to produce not only plasma, but also serum. In the prior art methods and apparatus, because of the severe handling requirements and other factors, an anticoagulant is present in the collection bag, thereby preventing the production or collection of serum without expensive and time consuming treatment of the collected plasma. In the present system, it is possible to collect either plasma by having an anticoagulant present in the collection bag 65, or to collect serum by not having an anticoagulant present in the collection bag. This flexibility is not available in prior art systems and is a distinct feature of the present invention.

While the present invention has been described in connection with a system for collecting blood plasma, it is understood and intended to be included in the present invention that other blood fractions may be collected, such as ultrafiltrates of salt and water and various proteins such as immune globulins.

Further, while the fractionator 55 is shown in situ on a blood donor 51, that is, providing a continuous flow path between the blood donor's vessels 63 and 73, it is contemplated that the fractionator may be used outside of such system. For instance, the fractionator 55 may be used to produce plasma or other blood fractions from blood previously obtained in batch fashion.

It is seen that the system, method and apparatus disclosed herein fractionates blood at a rapid rate, producing blood fractions at a rapid rate. The system can be operated in situ to produce the blood fraction continuously without alteration of the system after it is operating. The system, as applied to human donors, reduces the risk of infection and blood exchange as compared to presently used plasma collection systems. While there has been described herein what at present is considered to be the preferred embodiment of the present invention, various modifications and alterations can be made therein without departing from the true spirit and scope of the present invention, and it is intended to cover in the appended claims all such modifications and alterations.

What is claimed is:

1. Apparatus for continuously fractionating blood comprising a housing having a blood inlet adapted to be connected to a blood source and a blood outlet in fluid communication with said blood inlet and a blood fraction outlet; a semipermeable membrane separating said blood fraction outlet from said blood inlet and outlet and permitting a blood fraction to pass therebetween, and means providing a plurality of high velocity jets of blood directed toward and along substantially one entire surface of said membrane to maintain said membrane sufficiently cake free for passage of blood fraction therethrough, passage of blood from said blood inlet along said membrane to said blood outlet continuously passing the blood fraction through said membrane and out of said blood fraction outlet.

2. The apparatus of claim 1, wherein said blood inlet and said blood outlet are on opposite sides of said housing and the blood flow path is substantially straight.

3. The apparatus of claim 1, wherein said blood inlet and said blood outlet are coaxial.

4. The apparatus of claim 1, wherein the effective membrane area is less than about sixteen square centimeters.

5. The apparatus of claim 1, wherein the blood flow path along said membrane has a depth measured perpendicularly from said membrane not greater than about 20 mils.

6. The apparatus of claim 1, wherein said semipermeable membrane has a pore size in the range of between about 0.1 microns and about 6 microns.

7. The apparatus of claim 1, wherein said means providing high velocity blood jets includes blood accelerating mechanism for providing blood flow velocities through said jets in the range of from about 40 cm/sec to about 80 cc/sec.

8. Apparatus for continuously fractionating blood comprising a first member having a blood inlet and a blood outlet, a shallow cavity in one surface of said first member in fluid communication with said blood inlet, a blood inlet manifold in said one surface of said first member intermediate said blood inlet and said shallow cavity having the same dimension transverse to blood flow between said inlet and outlet as said shallow cavity and being substantially deeper than said shallow cavity, a blood outlet manifold in said one surface of said first member having substantially the same dimensions as said blood inlet manifold, a second member having a cavity in one surface thereof in at least partial registry with said shallow cavity in said first member and having a blood fraction outlet in fluid communication therewith, a semipermeable membrane separating said shallow cavity in said first member from said cavity in said second member and permitting a blood fraction to pass therebetween, and means providing high velocity blood jets directed toward and along one surface of said semipermeable membrane to maintain said membrane sufficiently cake free for passage of the blood fraction therethrough, passage of blood from said blood inlet through said inlet manifold along said membrane to said blood outlet continuously passing the blood fraction through said membrane into said cavity in said second member to said blood fraction outlet.

9. The apparatus of claim 8, wherein said first member and said second members are rigid plates.

10. The apparatus of claim 8, wherein the major axes of said manifolds are parallel and said blood inlet and outlet are normal thereto at the midpoint thereof.

11. The apparatus of claim 8, wherein said shallow cavity is less than about 20 mils in depth.

12. The apparatus of claim 8, wherein said blood inlet manifold and said blood outlet manifold have a depth at least 10 times greater than said shallow cavity.

13. The apparatus of claim 8, wherein said shallow cavity extends substantially between said blood inlet and outlet manifolds.

14. The apparatus of claim 8, and further comprising a membrane support associated with said membrane preventing deflection thereof into said cavity in said second member.

15. The apparatus of claim 14, wherein said membrane support is in said cavity in said second member.

16. The apparatus of claim 8, and further comprising a blood fraction outlet manifold in said second member in fluid communication with said cavity and said blood fraction outlet.

17. The apparatus of claim 16, wherein said blood fraction outlet manifold has substantially the same dimensions as said blood outlet manifold and is in substantial registry therewith.

18. Apparatus for continuously fractionating blood comprising a first member having a blood inlet and a blood outlet, a shallow cavity having a depth not greater then about 20 mils in one surface of said first member in fluid communication with said blood inlet, a blood inlet manifold in said one surface of said first member intermediate said blood inlet and said shallow cavity having the same dimension transverse to blood flow between said inlet and outlet as said shallow cavity and being substantially deeper than said shallow cavity, a blood outlet manifold in said one surface of said first member having substantially the same dimensions as said blood inlet manifold, a second member having a cavity in one surface thereof in at least partial registry with said shallow cavity in said first member and having a blood fraction outlet in fluid communication therewith, a semipermeable membrane separating said shallow cavity in said first member from said cavity in said second member and permitting a blood fraction to pass therebetween, and an apertured plate intermediate said first member and said membrane such that blood flow between said blood inlet and said blood outlet through said apertured plate provides high velocity blood jets directed toward and along one surface of said membrane, blood flow along said membrane being turbulent and maintaining said membrane sufficiently cake free for passage of the blood fraction therethrough, passage of blood from said blood inlet through said inlet manifold and said plate along said membrane to said blood outlet continuously passing the blood fraction through said membrane into said cavity in said second member to said blood fraction outlet.

19. The apparatus of claim 18, wherein said plate has an enlarged opening therein in registry with said blood outlet manifold.

20. The apparatus of claim 18, wherein said apertures in said plate distributing blood toward said membrane have diameters less than about 20 mils.

21. The apparatus of claim 18, wherein said apertures are arranged in rows and columns substantially uniformly across said plate surface.

22. The apparatus of claim 18, wherein at least some of said apertures in said plate form an angle other than normal to the plate surface.

23. The apparatus of claim 18, wherein at least some of said apertures in said plate are angularly disposed such that blood flowing therethrough impinges said membrane at an angle other than normal to said membrane and in a direction toward said blood fraction outlet.

24. The apparatus of claim 18, wherein said apertured plate has an area substantially coextensive with said membrane.

25. The apparatus of claim 18, wherein all of said apertures directing blood toward said membrane are normal to the plate surface.

26. The apparatus of claim 18, wherein said apertured plate thickness is less than about 30 mils.

27. A system for continuously fractionating blood in situ comprising a housing having a blood inlet adapted to be connected to a blood vessel and a blood outlet adapted to be connected to a blood vessel and a blood fraction outlet adapted to be connected to a collecting means, a semipermeable membrane separating said blood fraction outlet from said blood inlet and outlet and permitting a blood fraction to pass therebetween, means including blood flow accelerating mechanism providing high velocity blood jets directed toward and along substantially one entire surface of said membrane to maintain said membrane sufficiently cake free for continuous passage of the blood fraction therethrough, passage of blood from said blood inlet to said blood outlet along said membrane continuously providing the blood fraction collected in said collecting means.

28. The system of claim 27, wherein said accelerating means includes a blood pump intermediate said blood inlet and the vessel connected thereto.

29. The system of claim 28, and further comprising a blood clot filter intermediate said blood pump and said blood inlet.

30. The system of claim 27, and further comprising a blood clot filter intermediate said blood outlet and the associated blood vessel.

31. The system of claim 27, wherein said blood flow accelerating mechanism provides a blood flow velocity through said housing in the range of between about 40 cm/sec and about 80 cm/sec.

32. The system of claim 27, wherein the effective length of the blood flow path from said blood inlet to said blood outlet is less than about 4 inches.

33. The system of claim 27, wherein the effective length of the blood flow path from said blood inlet to said blood outlet is about 2 inches.

34. The system of claim 27, wherein the blood flow along said membrane is in a channel having a depth measured perpendicularly from said membrane of about less than about 20 mils.

35. A process for continuously fractionating blood comprising providing a blood flow path defined partially by one surface of a semipermeable membrane having a pore size from about 0.1 to about 6 microns in diameter, providing high velocity blood jets directed toward and along substantially one surface of the membrane sufficient to maintain the one surface sufficiently cake free for continuous passage of a blood fraction therethrough, collecting the blood fraction passing through the one surface of the membrane, and recovering the remaining blood components unable to pass through the membrane.

36. The process set forth in claim 35, wherein the flow path defined by the membrane surface has a depth measured vertically therefrom of less than about 20 mils.

37. The process set forth in claim 35, wherein the blood flow velocity in the blood flow path is in the range of from about 40 cm/sec to about 80 cm/sec.

38. The process set forth in claim 35, wherein the blood fraction flow rate through the membrane is between about 20 and 30 percent by volume of the blood flow rate past the membrane.

39. A process for continuously fractionating blood in situ comprising continuously directing blood from a donor along a blood flow path at least partially defined by one surface of a semipermeable membrane having a pore size from about 0.1 to about 6 microns in diameter, providing high velocity blood jets directed toward and along substantially one entire surface of the membrane sufficient to maintain the one surface sufficiently cake free for continuous passage of a blood fraction therethrough, continuously collecting the blood fraction passing through the one surface of the membrane, and continuously directing the remaining blood components back to the donor.

40. The process set forth in claim 39, wherein the membrane pore size is between about 2 and about 5 microns in diameter and the blood fraction is plasma.

41. The process set forth in claim 39, wherein the blood flow path is substantially straight.

42. The process set forth in claim 39, wherein the blood flow path defined by the membrane surface is less than about 2 inches in length.

43. The process set forth in claim 39, wherein the blood flow path defined by the membrane surface has a depth measured vertically therefrom of less than about 20 mils.

44. The process set forth in claim 39, wherein the blood fraction flow rate through the membrane is between about 20 and about 30 percent by volume of the blood flow rate past the membrane.

45. The process set forth in claim 39, wherein the blood flow rate is in the range of from about 75 cc/minute to about 150 cc/minute.

46. The proess set forth in claim 39, wherein the volume of the blood fraction passing through the membrane measured as a percentage of the blood flow rate past the membrane remains substantially constant.

47. The process set forth in claim 39, wherein the blood fraction is serum.

48. A process for continuously fractionating blood in situ from a donor and returning a portion of the blood to the donor while extracting a blood fraction, comprising providing a blood flow path defined partially by one surface of a semipermeable membrane having a pore size from about 0.1 to about 6 microns in diameter, accelerating the blood to a velocity at least about 40 centimeters per second and directing the high velocity blood against the membrane for continuous passage of a blood fraction therethrough, collecting the blood fraction passing through the membrane, and recovering the remaining portion of the blood unable to pass through the membrane and returning same to the donor.

49. The process of claim 48, wherein the blood fraction is plasma.

50. The process of claim 48, wherein the blood is accelerated by passing blood through an apertured plate.

51. The process of claim 50, wherein substantially all of the blood accelerated to a high velocity is directed toward the membrane and the one surface of the membrane is substantially flat.

* * * * *